(12) United States Patent
Benavitz

(10) Patent No.: US 9,801,621 B2
(45) Date of Patent: Oct. 31, 2017

(54) ARTHROSCOPIC BICEPS TENODESIS IN CONTINUITY

(71) Applicant: Arthrex, Inc., Naples, FL (US)

(72) Inventor: William C. Benavitz, Naples, FL (US)

(73) Assignee: Arthrex, Inc., Naples, FL (US)

( * ) Notice: Subject to any disclaimer, the term of this patent is extended or adjusted under 35 U.S.C. 154(b) by 324 days.

(21) Appl. No.: 14/604,237

(22) Filed: Jan. 23, 2015

(65) Prior Publication Data
US 2015/0201925 A1    Jul. 23, 2015

Related U.S. Application Data

(60) Provisional application No. 61/930,652, filed on Jan. 23, 2014.

(51) Int. Cl.
*A61B 17/04* (2006.01)
*A61F 2/08* (2006.01)

(52) U.S. Cl.
CPC ........ *A61B 17/0401* (2013.01); *A61F 2/0805* (2013.01); *A61F 2/0811* (2013.01); *A61B 17/0485* (2013.01); *A61B 2017/044* (2013.01); *A61B 2017/0445* (2013.01); *A61F 2002/0858* (2013.01); *A61F 2002/0888* (2013.01)

(58) Field of Classification Search
CPC ............ A61B 17/0401; A61B 17/0485; A61B 2017/044; A61B 2017/0445; A61B 17/00; A61F 2/0805; A61F 2/0811; A61F 2002/0858; A61F 2002/0888; A61F 2002/0847; A61F 2002/0876; A61F 2/00; A61F 2/02

USPC ........................................................ 606/232
See application file for complete search history.

(56) References Cited

U.S. PATENT DOCUMENTS

| | | |
|---|---|---|
| 2003/0050666 A1 | 3/2003 | Grafton |
| 2004/0093031 A1 | 5/2004 | Burkhart et al. |
| 2005/0192631 A1 | 9/2005 | Grafton |
| 2006/0259076 A1 | 11/2006 | Burkhart et al. |
| 2007/0135843 A1 | 6/2007 | Burkhart |
| 2008/0004659 A1 | 1/2008 | Burkhart et al. |
| 2014/0046369 A1* | 2/2014 | Heaven ............. A61B 17/0401 606/232 |

OTHER PUBLICATIONS

John L. Eakin, James R. Bailey, Chris B. Dewing, Joseph R. Lynch, Matthew T. Provencher, Subpectoral Biceps Tenodesis, Sep. 2012, Department of Orthopedic Surgery, Naval Medical Center San Diego, Operative Techniques in Sports Medicine, vol. 20, Issue 3, pp. 244-252.*

* cited by examiner

*Primary Examiner* — Christopher L Templeton
*Assistant Examiner* — George J Ulsh
(74) *Attorney, Agent, or Firm* — Blank Rome LLP

(57) ABSTRACT

Techniques and reconstruction systems for soft tissue surgical repairs. The biceps tenodesis technique of the present invention provides fixation of a single diameter of the biceps tendon in a socket without the need for externalizing the tendon and without the need to pass any suture (or similar material) through any portion of the tendon (i.e., without the need to stitch or whipstitch any area/portion of the tendon). The technique improves the biomechanics of the combined fixation and helps overcome surgeons' concerns about rapid return to ADLs.

12 Claims, 7 Drawing Sheets

ARTHROSCOPIC BICEPS TENODESIS IN CONTINUITY

CROSS-REFERENCE TO RELATED APPLICATIONS

This application claims the benefit of U.S. Provisional Application No. 60/930,652, filed Jan. 23, 2014, the entire disclosure of which is incorporated by reference herein.

FIELD OF THE INVENTION

The present invention relates to the field of surgery and, more specifically, to tendon repairs for reconstructive surgeries.

BACKGROUND OF THE INVENTION

A common type of biceps tendon tear is detachment (partial or complete) of one of the biceps tendons within the shoulder joint. There are two attachments of the biceps tendon at the shoulder, one within the shoulder joint (the long head of the biceps) and the other in front of the shoulder joint (the short head of the biceps). Injuries to the proximal biceps tendon almost always involve the long head of the biceps. When the long head of the biceps tendon is damaged, a treatment that may be considered is biceps tenodesis.

A biceps tenodesis procedure involves cutting the long head of the biceps just prior to its insertion on the superior labrum and then anchoring the tendon along its anatomical course more distally along the humerus. A number of different anchoring techniques are currently used by surgeons. These techniques include fixation devices such as cortical buttons, bio-tenodesis screws and suture anchors. The key to performing a biceps tenodesis is moving the tendon from its normal attachment within the shoulder joint to a new location further down the humerus. An optimal technique would be characterized by limited anterior incisions, early range of motion due to strength and gapping of the repair, and minimum complications.

There is a need for improved methods of attachment of the biceps tendon outside of the shoulder joint that can cause fewer problems within the joint. Also needed are methods and devices that provide fixation of the biceps tendon in a socket without the need for externalizing the tendon and without the need to stitch (whipstitch) the tendon.

SUMMARY OF THE INVENTION

The method of the present invention provides improved methods of biceps tenodesis that are conducted arthroscopically and that provide fixation of a single diameter of the biceps tendon in a socket without the need for externalizing the tendon and without the need to stitch (whipstitch) the tendon.

These and other features and advantages of the invention will be more apparent from the following detailed description that is provided in connection with the accompanying drawings and illustrated exemplary embodiments of the invention.

DETAILED DESCRIPTION OF THE PREFERRED EMBODIMENTS

Figure 1:
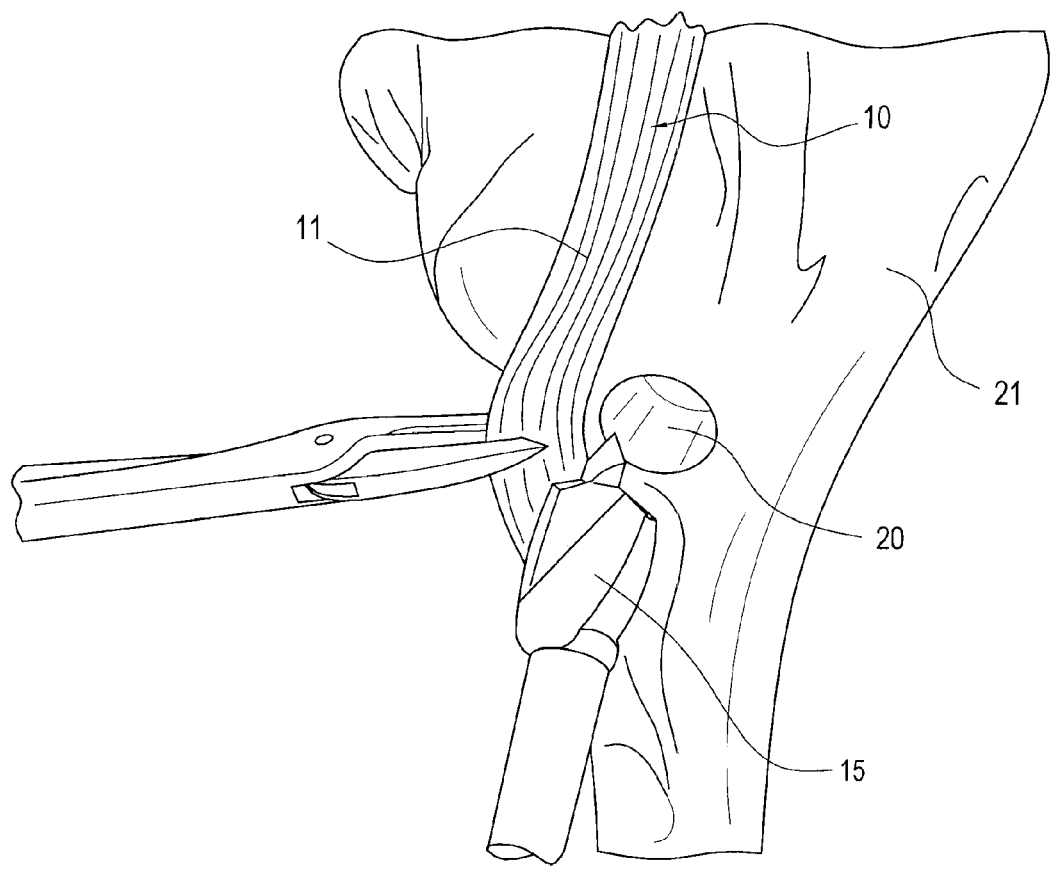
FIGS. 1-8 illustrate subsequent steps of a method of biceps tenodesis of the present invention.

In the following detailed description, reference is made to various specific embodiments in which the invention may be practiced. These embodiments are described with sufficient detail to enable those skilled in the art to practice the invention, and it is to be understood that other embodiments may be employed, and that structural changes may be made without departing from the scope of the present invention.

The technique of the present invention improves the biomechanics of the overall biceps tenodesis repair and helps overcome surgeons' concerns about rapid return to ADLs. The technique reliably seats the tendon within the bone socket, without the need to expose the tendon externally and without the need to whipstitch the tendon. The technique restores the anatomical footprint and provides the optimal strength and biomechanical characteristics to allow immediate active range of motion. The method of the present invention provide fixation of a single diameter of the biceps tendon in a socket without the need for externalizing the tendon and without the need to stitch (whipstitch) the tendon, i.e., without the need to pass any suture (or similar material) through any portion of the tendon.

The present invention also provides a method of tendon repair by inter alia the steps of: (i) exposing a native tendon attached to an extremity of a patient; (ii) providing a tunnel or socket into the bone on which the native tendon is attached; (iii) passing a flexible strand around the tendon to form a loop and two tails, the loop extending around the tendon; (iv) feeding the two tails through an eyelet of a knotless fixation device and pulling on the two tails to form a noosed loop around the tendon; (v) cutting the tendon at a location between the noosed loop and a most distal end of the tendon with a noosed end; and (vi) securing the noosed end of the cut tendon into the tunnel or socket by employing the knotless fixation device.

The present invention also provides a method of biceps repair by inter alia the steps of: (i) exposing a native biceps attached to an extremity of a patient and identifying a long head of the biceps; (ii) forming a socket into the bone on which the biceps is attached; (iii) passing a flexible strand around the biceps to form a loop and two tails/limbs, the loop extending around the biceps so that the loop surrounds the biceps but does not pass through the biceps; (iv) threading the two tails/limbs through an eyelet or aperture of a knotless fixation device, and pulling on the two tails to form a noosed loop around the biceps and to tension the flexible strand around the biceps; (v) cutting the biceps at a location between the noosed loop and a most distal end of the biceps with a noosed end, and above 2-3 mm above the noosed loop; and (vi) securing the noosed end of the cut biceps into the socket by employing the knotless fixation device.

The present invention also provides a method of biceps tendon repair by inter alia the steps of: (i) conducting an incision to a joint of a patient to expose a long head of biceps tendon, the biceps tendon being attached to an extremity of the patient; (ii) identifying the long head of the biceps tendon and exposing the long head of the biceps tendon without externalizing the biceps tendon; (iii) forming a socket into the bone on which the biceps tendon is attached; (iv) passing a flexible strand around the long head of the biceps tendon to form a loop and two tails or limbs, the loop surrounding the long head of the biceps tendon without passing through any portion of region of the biceps tendon; (iv) feeding the two tails or limbs through an eyelet, aperture or tip of a knotless construct, the knotless construct having a cannulated fixation device (for example, an implant such as a cannulated plug or screw) and an eyelet, aperture or tip; (v) pulling on the two tails or limbs to tension the tails or limbs and to form a noosed loop around the long head of the biceps tendon, the noosed loop having a diameter smaller than a diameter of the loop; (vi) cutting the long head of the biceps tendon at a location between the noosed loop and a most distal end of the biceps, and above 2-3 mm above the noosed loop, to obtain a noosed end; (vii) inserting the noosed end of the cut biceps tendon into the socket into the bone; and (viii) advancing the cannulated fixation device into the socket and over the noosed end. to secure the noosed end of the cut biceps tendon into the socket.

As detailed below, the present invention employs a cut native tendon that has a noosed end and wherein tails are fed through an aperture of a knotless construct which secures the cut native tendon into a bone socket. The knotless construct is a fixation device which may be provided with an anchor tip having an eyelet or aperture (that allows passing of at least one flexible strand through it) and a cannulated fixation device (for example, an implant such as a cannulated plug or screw) that secures the anchor tip and eyelet with attached flexible strand into a bone hole/socket. The cannulated fixation device (implant) can be inserted into the bone after the anchor tip has been implanted and/or after the flexible strand (suture) of the eyelet has been tensioned.

In an exemplary-only embodiment, the knotless construct is a two-piece construct (a two-piece anchor) such as Arthrex PushLock® anchor, disclosed in U.S. Pat. No. 7,329,272, the disclosure of which is incorporated by reference in its entirety herewith. In yet additional embodiments, the knotless construct may be a swivel anchor used to capture a flexible strand (suture, suture tape or suture chain) for surgical tissue repair without requiring suture knots, as disclosed and described in U.S. Patent Publication No. 2008/0004659, the disclosure of which is incorporated by reference in its entirety herewith. The implant (swivel anchor or SwiveLock™ C anchor) includes a closed aperture/eyelet or a forked tip to allow free sliding of a suture strand or capturing of a suture chain. The swivel anchor is secured in a hole in bone by advancing a fixation device (such as a cannulated interference screw or plug) over the body of the implant.

Exemplary methods of a biceps tenodesis technique of the present invention to obtain soft tissue repair 100 are detailed below with reference to FIGS. 1-8. For simplicity, the steps below will be made with reference to repair of a native biceps (biceps tendon); however, the invention is not limited by this exemplary-only embodiment and has applicability to any type of soft tissue attached to an extremity of a patient (naturally attached to bone) and that can be exposed at a joint.

The biceps tenodesis technique of the present invention provides fixation of a single diameter of the biceps tendon in a socket without the need for externalizing the tendon and without the need to pass any suture (or similar material) through any portion of the tendon (i.e., without the need to stitch or whipstitch any area/portion of the tendon).

FIG. 1: Step 1: Expose the biceps 10 and reflect away from the bicipital groove with a grasper. Make the appropriate size pilot socket 20 with a cutting instrument 15, for example, a reamer such as Arthrex Pilot Headed Reamer.

Figure 2:
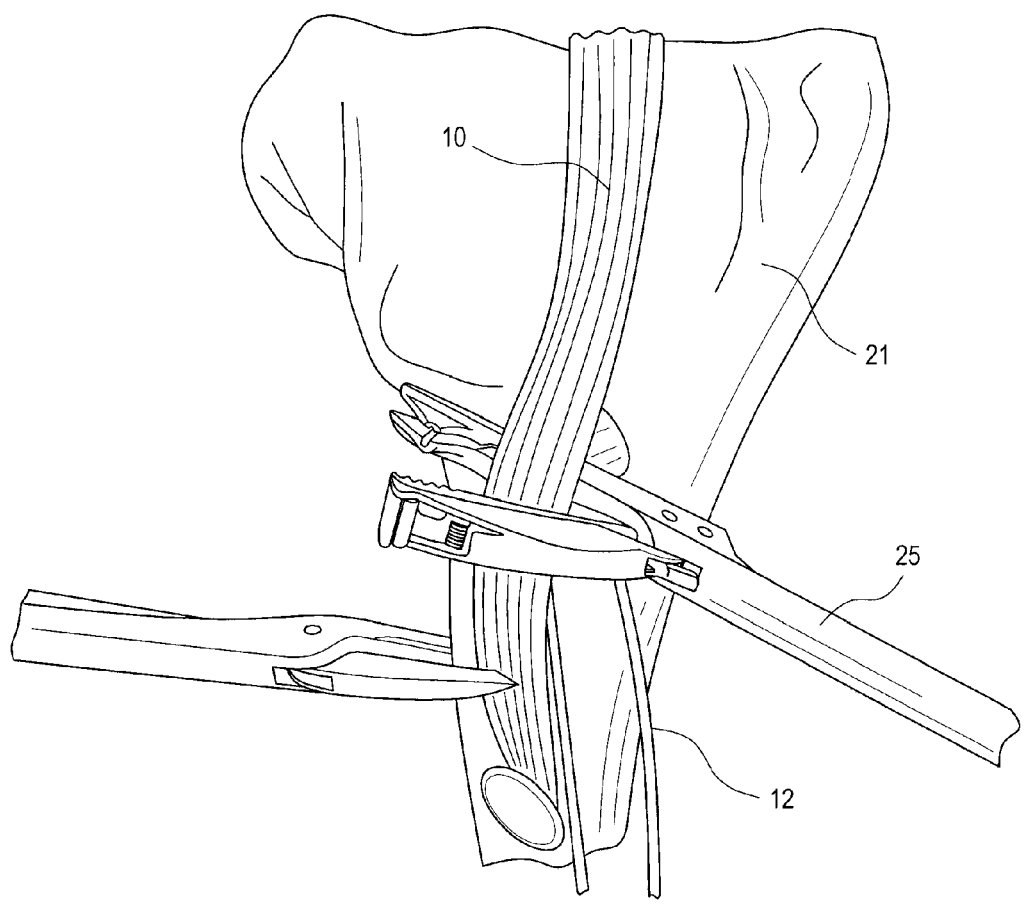

FIG. 2: Step 2: Using a suture passing instrument 25, such as a Scorpion Suture Passer, pass a flexible strand 12 (for example, suture such as a #2 FiberWire® suture) around the biceps 10 to form loop 13 (FIG. 3) and tails or limbs 12a, 12b.

Figure 3:
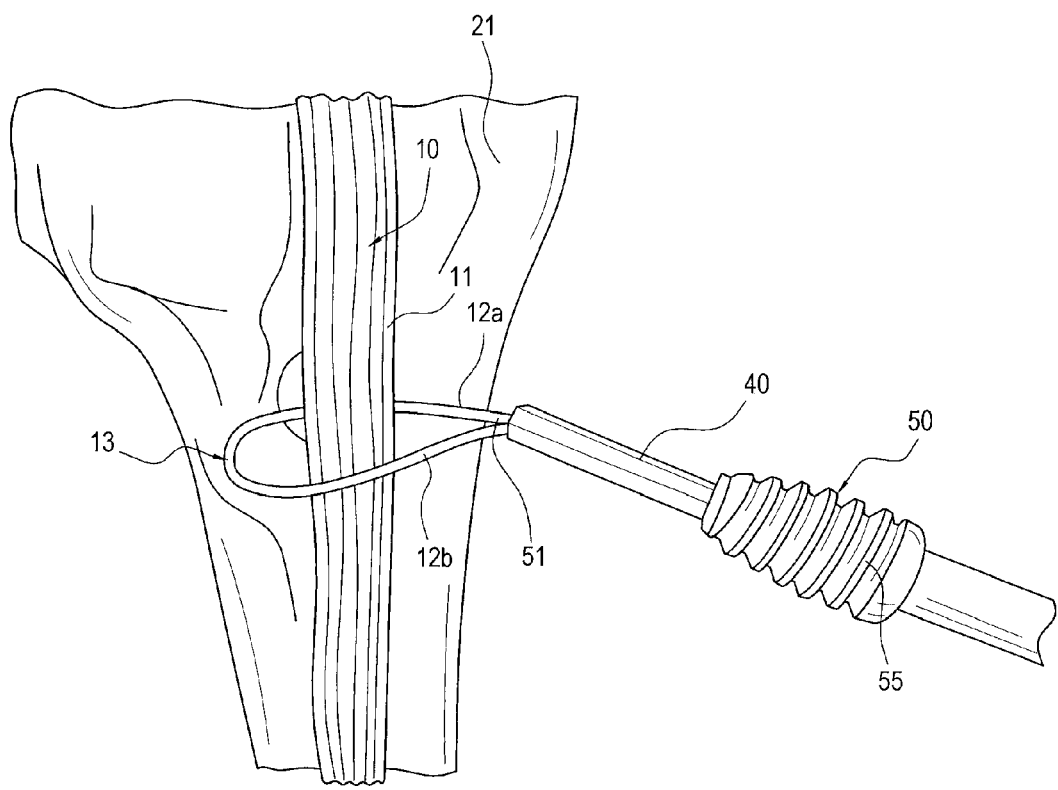

FIG. 3: Step three: Both tails 12a, 12b of the FiberWire® suture 12 that were passed around the biceps tendon 10 are retrieved through an arthroscopic portal/cannula. These tails 12a, 12b are then fed through an eyelet or tip 51 (with eyelet 52) of a knotless fixation device 50 such as a SwiveLock® anchor or a PushLock® anchor, provided with an anchor body 55 (which may be a screw such as a cannulated interference screw or tenodesis screw) that is inserted over a cannulated shaft of a driver 40 and advanced to be fully seated on the driver tip. The tip 51 may be configured to rotate or swivel relative to the driver shaft and the anchor body (screw). The driver may be a reusable or disposable tenodesis driver having attached tenodesis screw 55.

Figure 4:
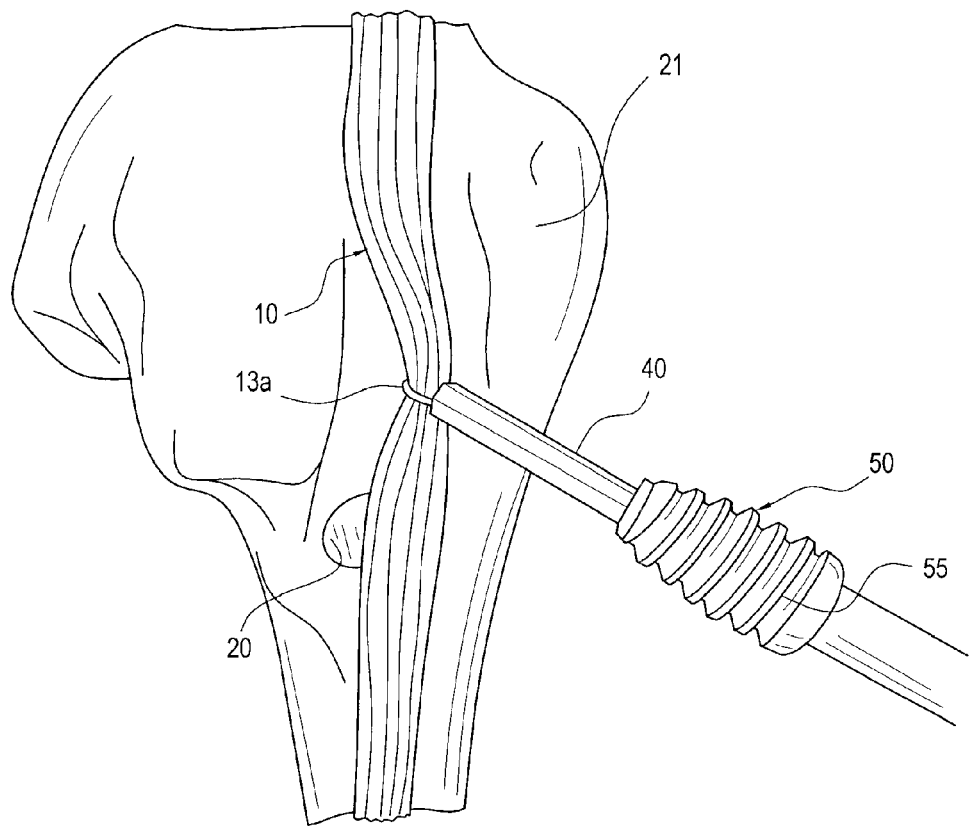

FIG. 4: Step 4: Push the driver/implant 40/50 through the arthroscopic portal while taking out slack from the FiberWire® suture 12 that is noosed around the biceps tendon 10. Position the noose/loop 13a approximately 15 mm proximal to the socket 20 that was previously prepared. Tighten the noose/loop 13a and use a hemostat on the back of the driver to secure.

Figure 5:
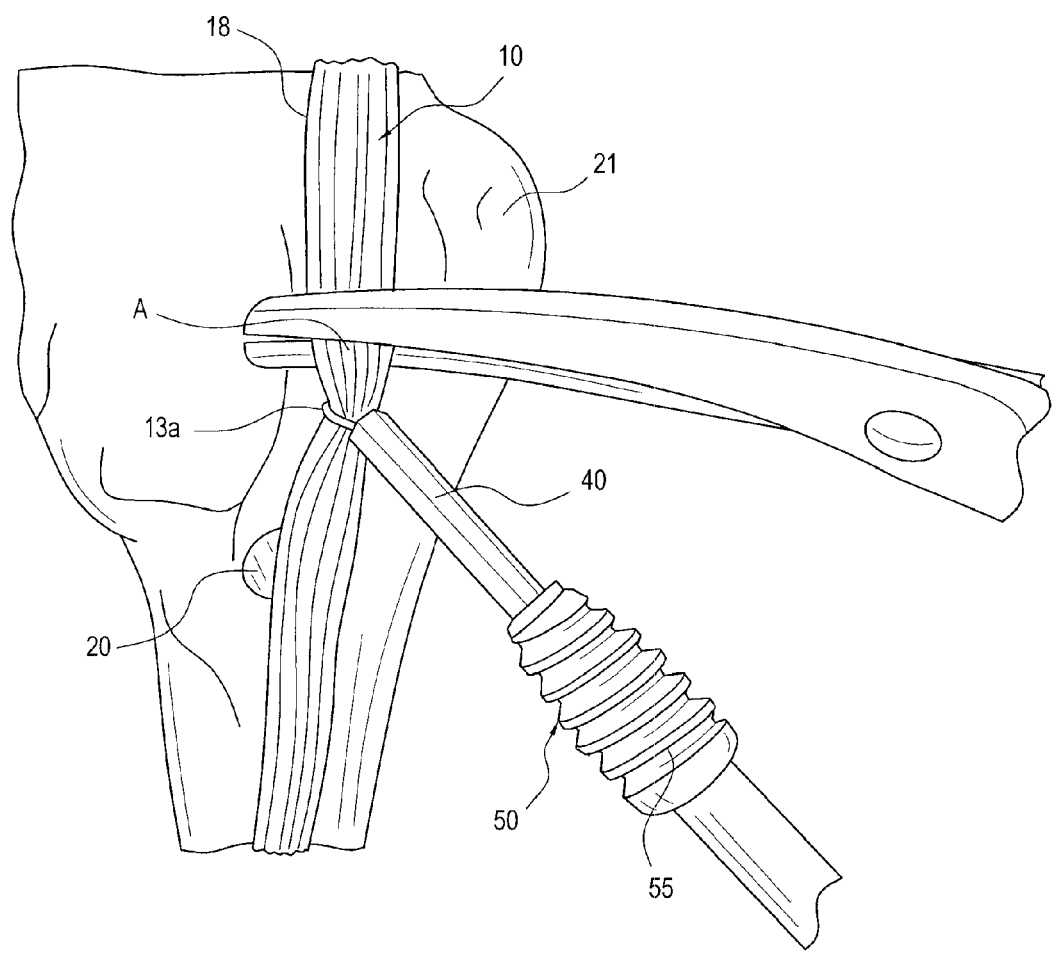

FIG. 5: Step five: Using the arthroscopic portal and arthroscopic scissors or cautery, cut the biceps tendon 10 at a location A and approximately 2-3 millimeters above the noose/loop 13a (to obtain cut biceps 10b with noosed end 10a, shown in FIG. 6). Noosed loop 13a is located at a distance of about 2-3 mm from a most distal end of the noosed end 10a.

Figure 6:
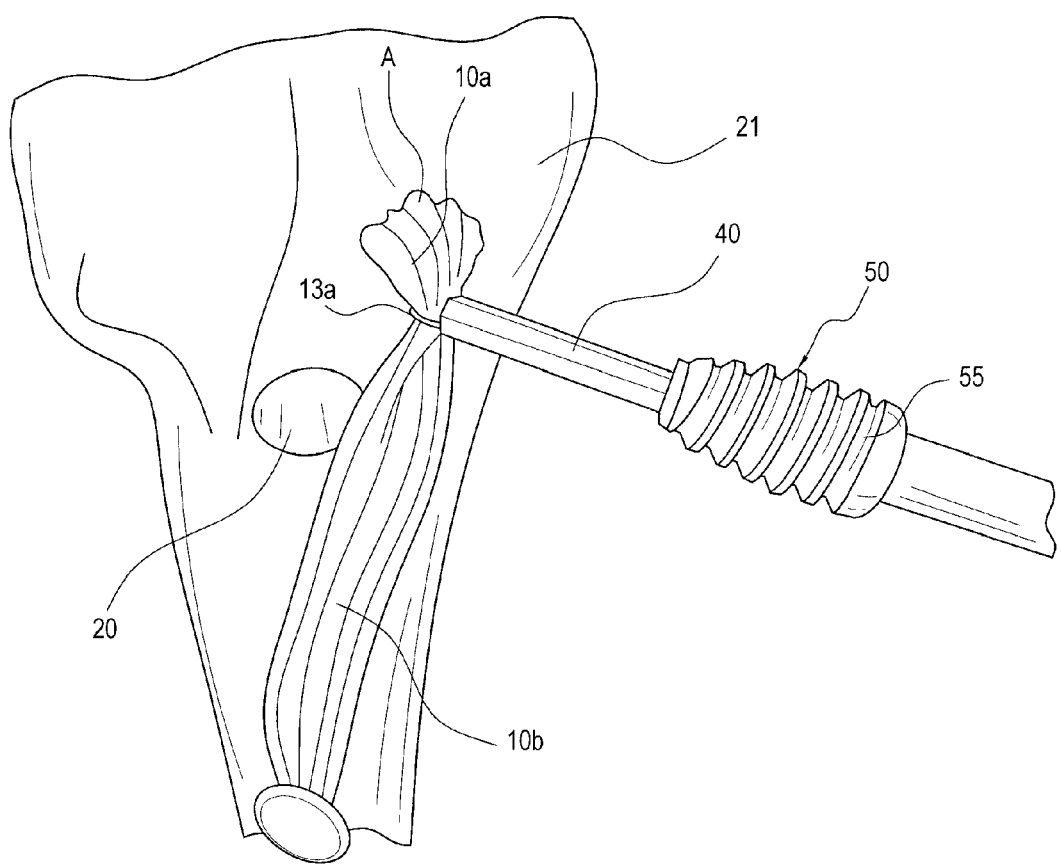

FIG. 6: Step six: Maneuver the grasped end of the cut biceps 10a into the previously prepared bone socket 20.

Figure 7:
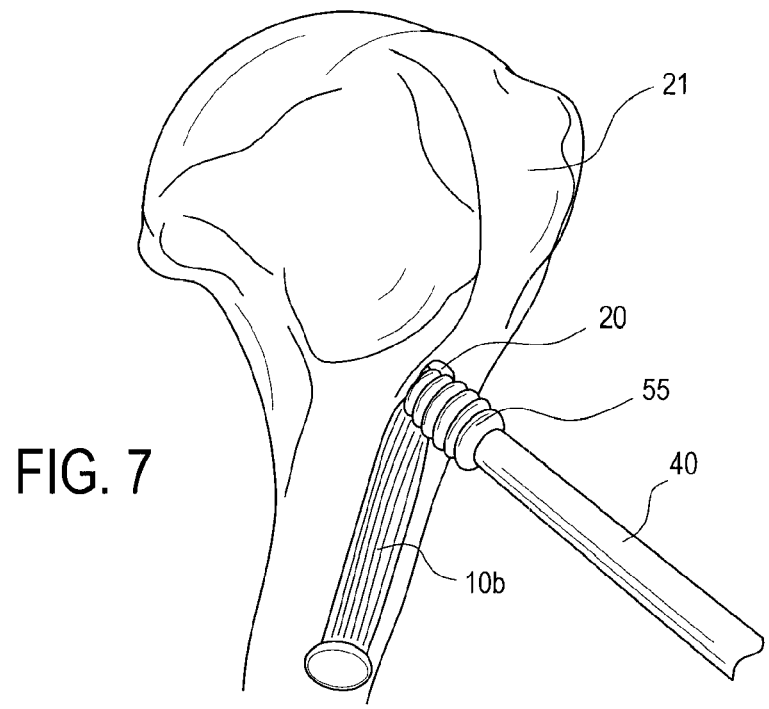
Figure 8:
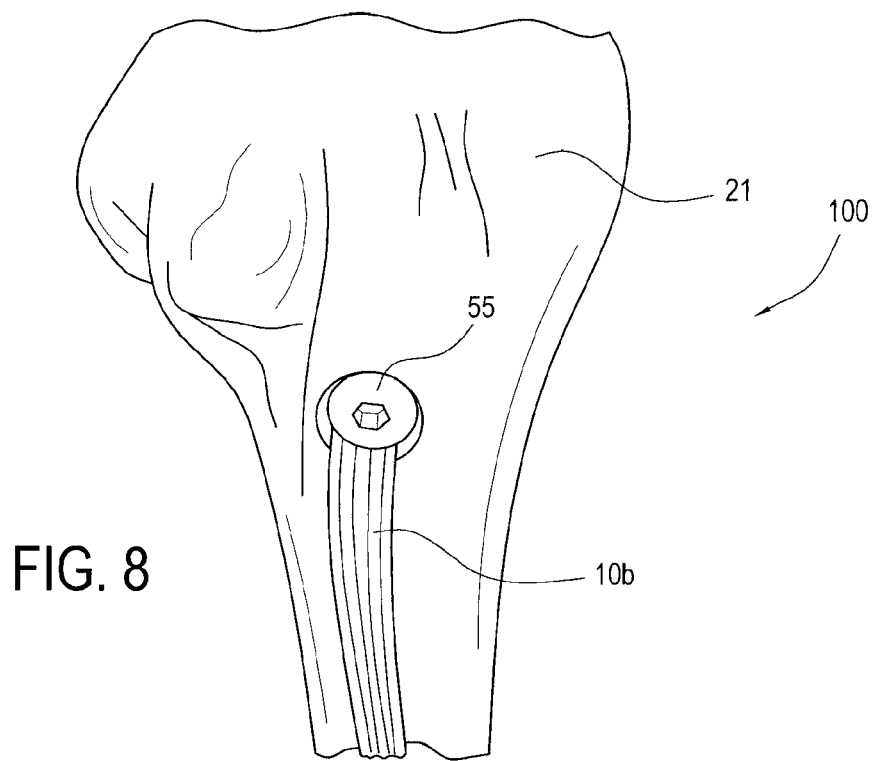

FIGS. 7 and 8: Step seven: With the tip of the driver and the noosed end 10a of the biceps 10b pushed into the previously prepared bone socket 20, the screw 55 is advanced with the driver thumb pad until the anchor 55 is just flush with the bone surface. Remove driver and cut suture to obtain biceps repair 100 (FIG. 8).

The present invention provides a method of arthroscopic biceps tenodesis in continuity by inter alia the steps of (i) exposing a long head 11 of a biceps tendon 10 attached to an extremity of a patient; (ii) forming a socket 20 into humerus 21 on which the biceps tendon is attached; (iii) passing a flexible strand 12 around the long head 11 of the biceps tendon 10 to form a loop 13 and two tails or limbs 12a and 12b, the loop 13 surrounding the long head 11 of the biceps tendon 10; (iv) feeding/threading the two tails or limbs 121a, 12b through an eyelet 52 or tip 51 of a knotless construct 50, the knotless construct 50 having a cannulated fixation device 55 (for example, an implant such as a cannulated plug or screw) and an eyelet or tip 51; (v) pulling on the two tails or limbs 12a, 12b to form a noosed loop 13a around the long head 11 of the biceps tendon 10, the noosed loop 13a having a diameter smaller than a diameter of the loop, and to tension the two tails to limbs 12a, 12b and the noosed loop 13a; (vi) cutting the long head 11 of the biceps tendon 10 at a location A between the noosed loop 13a and a most distal end 18 of the biceps, and above 2-3 mm above the noosed loop 13a, to obtain a noosed end 10a as part of a cut biceps tendon 10b; (vii) inserting the noosed end 10a of the cut biceps tendon 10b into the socket 20 into the bone 21; and (viii) advancing the cannulated fixation device 55 into the socket, and over the noosed end 10a, to secure the noosed end 10a of the cut biceps tendon 10b into the socket 20.

As noted, knotless construct 50 may be an exemplary two-piece anchor such as Arthrex PushLock® anchor, disclosed in U.S. Pat. No. 7,329,272, the disclosure of which is incorporated by reference in its entirety herewith. In an exemplary embodiment only, knotless construct 50 includes anchor tip 51 with eyelet 52 and cannulated fixation device 55 which secures the anchor tip 51 with eyelet (with at least one flexible strand 12 attached to it) into hole 20. Eyelet 52 may be an aperture or opening that allows at least one flexible strand 12 (for example, one or more sutures 12) to slide therethrough. A plurality of barbs or threads may be provided on the outer surface of anchor tip to facilitate the insertion of the anchor tip within bone socket or hole 20.

Cannulated fixation device 55 may be an implant such as a cannulated plug or screw, as disclosed in U.S. Pat. No. 7,329,272, the disclosure of which is incorporated in its entirety by reference herewith. An impactor or cannulated tamp can be employed to advance the fixation device 55 into the bone hole 20.

The surgical repairs of the present invention may employ any type of flexible material or suture 12, for example FiberWire® or FiberTape® or FiberChain®. In another embodiment, an allograft or biological component may be used together with suture or tape. The allograft or biological component may be comprised of tendon or pericardium, for example, which provides improved tissue repair. In yet additional embodiments, any combination of suture, suture tape, suture chain, and allograft or biological component may be employed, depending on the characteristics of the specific surgical repair and/or as desired.

Flexible strand or cord 12 may be made of any known suture construct, such as multifilament, braided, knitted, woven suture, or including fibers of ultrahigh molecular weight polyethylene (UHMWPE) or the FiberWire® suture (disclosed in U.S. Pat. No. 6,716,234, the disclosure of which is hereby incorporated by reference in its entirety herein). FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire® suture includes a core within a hollow braided construct, the core being a twisted yarn of UHMWPE.

The flexible strand 12 may be also in the form of flat suture tape (for example, a collagen stuffed suture tape or a high strength suture tape, such as disclosed in U.S. Pat. No. 7,892,256) or a combination of suture and tape, a stiff material, or combination of stiff and flexible materials, depending on the intended application. The flexible strand 12 may be also in the form of a suture chain described in U.S. Pat. No. 7,803,173 and/or in U.S. Patent Appl. Publ. No. 2007/0135843, the disclosures of both of which are incorporated by reference in their entirety herewith. The strands 12 may also be formed of a stiff material, or combination of stiff and flexible materials, depending on the intended application. The strands may be also coated and/or provided in different colors.

The tissue repairs of the present invention may be used in conjunction with any knotless fixation devices, for example, any of swivel and/or screw-in suture anchors and/or push-in suture anchors (such as an Arthrex SwiveLock® anchor, disclosed in U.S. Patent Application Publication No. 2008/0004659 or a PushLock® anchor, as disclosed in U.S. Pat. No. 7,329,272). The fixation devices may be also any anchors, implants or screws (such as interference screws or tenodesis screws) or any fixation element that allows attachment/fixation of the knotless suture construct to bone. The fixation devices/implants may have various sizes (various diameters and/or lengths) and may be formed of biocompatible materials such as PEEK, biocomposite materials, metals and/or metal alloys, or combination of such materials, among others.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed as new and desired to be protected by Letters Patent of the United States is:

1. A method of tendon repair, comprising the steps of:
forming a bone socket in a bone adjacent a native tendon, the native tendon being naturally attached to the bone;
exposing the native tendon;
passing a flexible strand around the native tendon using a suture passing instrument;
forming a loop with the flexible strand after the step of passing the flexible strand around the native tendon using the suture passing instrument, such that the loop surrounds the native tissue;
passing two tails of the loop through an eyelet of a knotless construct, the knotless construct comprising a cannulated fixation device and the eyelet that captures the flexible strand;
pulling on the two tails to form a noosed loop around the native tendon;
severing the native tendon at a location between the noosed loop and a most distal end of the native tendon to obtain a noosed end of the tendon; and
securing the noosed end of the tendon in the bone socket with the cannulated fixation device.

2. The method of claim 1, wherein the securing step comprises the steps of inserting the noosed end of the tendon into the bone socket and, subsequently, inserting the cannulated fixation device within the bone socket and adjacent the eyelet, to secure the noosed end of the tendon into the bone socket.

3. The method of claim 1, wherein the step of severing the tendon comprises the steps of determining a cutting location approximately 2-3 mm above the location of the noosed loop, and between the noosed loop and the most distal end of the native tendon, and then cutting the native tendon at the cutting location.

4. The method of claim 1, wherein the native tendon is biceps.

5. The method of claim 1, wherein the flexible strand is suture, suture tape or suture chain.

6. The method of claim 1, wherein the fixation device is an implant or screw.

7. The method of claim 1, wherein the flexible strand is formed of suture material comprising ultrahigh molecular weight polyethylene.

8. The method of claim 1, wherein the native tendon is repaired without passing any flexible strand through the native tendon.

9. The method of claim 1, wherein the native tendon is repaired without suturing or stitching any portion of the native tendon.

10. The method of claim 1, wherein the step of exposing the native tendon is conducted without externalizing the native tendon.

11. A method of arthroscopic biceps tenodesis in continuity, the method comprising the steps of:
exposing a native biceps without externalizing the native biceps;

passing a flexible strand around a long head of the native biceps using a suture passing instrument;

forming a loop with the flexible strand after the step of passing the flexible strand around the native tendon using the suture passing instrument, such that the loop surrounds the long head of the native tissue;

passing two tails of the loop through an eyelet or tip of a knotless construct, the knotless construct comprising a cannulated fixation device and the eyelet or tip that captures the flexible strand;

pulling on the two tails to form a noosed loop around the native biceps;

determining a cutting location on the long head of the native biceps, and between the noosed loop and a most distal end of the native biceps;

cutting the native biceps at the cutting location to sever the native biceps and to obtain a noosed end of the native biceps, a most distal end of the noosed end of the native biceps being located approximately 2-3 mm from the noosed loop;

inserting the noosed end into a socket formed into a humerus; and advancing the cannulated fixation device into the socket to secure the noosed end of the native biceps into the socket.

12. The method of claim 11 conducted without passing any flexible strand through the native biceps.

* * * * *